(12) United States Patent
Griffin et al.

(10) Patent No.: US 6,494,899 B1
(45) Date of Patent: Dec. 17, 2002

(54) PHOTOTHERAPY SYSTEM AND METHOD

(75) Inventors: Carl E. Griffin, Marietta, GA (US); Robert Whitaker, Marietta, GA (US); Robert Andersen, Marietta, GA (US)

(73) Assignee: Respironics, Inc., Murrysville, PA (US)

( * ) Notice: Subject to any disclaimer, the term of this patent is extended or adjusted under 35 U.S.C. 154(b) by 0 days.

(21) Appl. No.: 09/484,368

(22) Filed: Jan. 14, 2000

Related U.S. Application Data (60) Provisional application No. 60/116,837, filed on Jan. 22, 1999.

(51) Int. Cl.$^7$ ................................................ A61N 21/00
(52) U.S. Cl. ............................................ 607/88; 607/90
(58) Field of Search ............................ 607/88; 362/20, 362/572, 573; 606/2, 3, 10–12

(56) References Cited

U.S. PATENT DOCUMENTS

| | | |
|---|---|---|
| 1,073,192 A | 9/1913 | Warder |
| 2,195,374 A | 3/1940 | Wallace et al. |
| 3,577,173 A | 5/1971 | Blomgren |
| 4,399,358 A | 8/1983 | Burkhardt et al. |
| 4,410,929 A | 10/1983 | Feinbloom et al. |
| 4,461,974 A | 7/1984 | Chiu |
| 4,757,426 A | 7/1988 | Scheller et al. |
| 4,855,875 A | 8/1989 | Onose et al. |
| 4,975,810 A | 12/1990 | Venderbel |
| 5,008,548 A | * 4/1991 | Gat ............................ 250/372 |
| 5,178,446 A | * 1/1993 | Gruber et al. ................ 362/20 |
| 5,309,330 A | * 5/1994 | Pillars et al. ................. 362/32 |
| 5,311,410 A | * 5/1994 | Hsu et al. .................... 362/20 |
| 5,349,330 A | * 9/1994 | Diong et al. ................ 340/567 |
| 5,406,461 A | * 4/1995 | Amann ........................ 362/20 |
| 5,434,756 A | * 7/1995 | Hsu et al. .................... 362/32 |
| 5,676,452 A | * 10/1997 | Scholz ....................... 362/254 |
| 5,833,343 A | * 11/1998 | Nakano et al. ............... 362/20 |
| 6,185,356 B1 | * 2/2001 | Parker et al. ............... 385/133 |

* cited by examiner

*Primary Examiner*—Michael Peffley
*Assistant Examiner*—Pete J Vrettakos
(74) *Attorney, Agent, or Firm*—Michael W. Haas (57) ABSTRACT

A phototherapy system and method for automatically replacing a failed light source with a new light source once a failure of a first light source is detected. This system permits the new light source to assume a coaxially aligned position with the proximal end portion of a light transmission medium in place of the failed light source without any manual input by the user. In addition, an improved coupling system is provided for coupling the light transmission medium to the illumination device housing the light sources. The coupling system prevents pull out of the light transmission medium from the illumination device over nearly all rotational angles of the proximal end of the light transmission medium relative to the housing, and over only a relatively small range of angles will some degree of pull out force enable the light transmission medium to be decoupled from the illumination device.

11 Claims, 9 Drawing Sheets

PHOTOTHERAPY SYSTEM AND METHOD

CROSS-REFERENCE TO RELATED APPLICATIONS

This application claims priority under 35 U.S.C. §119(e) from U.S. provisional application No. 60/116,837 filed Jan. 22, 1999.

BACKGROUND OF THE INVENTION

1. Field of the Invention

The present invention pertains to a phototherapy system and method for providing a therapeutic light treatment to a patient, and, in particular, to a phototherapy system and method in which a bulb switching mechanism automatically replaces a failed bulb with a new bulb, and to a phototherapy system having an improved fiber optic cable coupling system.

2. Description of the Related Art

Phototherapy devices that generate radiant energy, typically a visible light having a particular wavelength, and that transmit the energy to a surface of a patient are known. In one type of phototherapy device, light from a halogen bulb is transmitted to the surface of the patient to treat jaundice. An example of such a conventional phototherapy device is the Wallaby® II phototherapy system distributed by Respironics Inc. of Pittsburgh, Pa.

Such conventional phototherapy devices typically include a source of illumination and a fiber optic cable having a proximal end coupled to the source of illumination for transmitting the light to the patient. A fiber optic panel is located at the distal end of the fiber optic cable to provide a blanket of light that can be positioned next to the patient's skin. A concern with such conventional devices is maximizing the lifetime of the device before the bulb or bulbs that produce the light have to be replaced.

This problem is addressed in conventional systems by providing two bulbs in the illumination device. If the first bulb fails, e.g., burns out, a manually actuated button is provided on the exterior housing of the illumination device. Depressing the button causes the second lamp, which is provided on a rotating carousel with the first lamp, to move into an operating position in place of the first lamp for illuminating the proximal end of the fiber optic cable. Thus, the user need not replace the bulbs until both bulbs have failed, thereby increasing the amount of time the phototherapy system can be used between bulb replacements.

This conventional approach, however, has several disadvantages. If the first bulb fails in the middle of the night, for example, while the patient is asleep, the patient or caregiver may not be aware of the failure until the following morning, thereby depriving the patient of the phototherapy during the night subsequent to the bulb failure. This problem is addressed in conventional device by providing an audible warning that is actuated upon bulb failure. Such warning devices, however, are a great cause for consternation, especially in situations where the user is unfamiliar with the purpose of the warning and/or is already apprehensive about the health of the person being treated by the phototherapy.

In addition, the conventional approach for dealing with bulb failures requires that the user manually cause the second bulb to move into position to replace the first bulb by actuating the bulb replacement button. Some patients may be unfamiliar with this procedure or have difficulty remembering to do so when the bulb replacement warning sounds. Also, some patients may have difficulty in being trained to take this necessary action once a bulb failure occurs. In addition, some patients may be physically unable to actuate the bulb replacement button, which requires depressing the bulb replacement button with a moderate amount of force sufficient to rotate the lamp carousel.

Furthermore, once the bulb replacement button has been actuated, the user cannot return the rotating carousel to the original position. Instead, the device must be delivered to a repair center where a trained technician replaces the bulbs and returns the carousel to the original position. As a result, if the user accidentally or prematurely causes the carousel to rotate, for example, by inadvertently depressing the bulb replacement button, the useful life of that device is effectively reduced. Yet another disadvantage with conventional phototherapy devices is that the mechanical rotation of the lamp carousel typically moves the lamps very rapidly and has an abrupt stop once the carousel has been rotated. This rapid movement and abrupt stop can cause mechanical shock to the filaments in the bulbs, thereby reducing lamp life.

Conventional phototherapy devices also include a system for coupling the proximal end of the fiber optic cable to the illumination device. The proximal end of the fiber optic cable receives light from the light source in the illumination device and transmits the therapeutic light to the distal end of the fiber optic cable for transmission to the patient's skin. The coupling system attaches the proximal end of the fiber optic cable to the illumination device so that the proximal end surface of the fiber optic bundle is situated a fixed distance from the light source to receive light from the light source. Conventional coupling systems also permit the fiber optic cable to rotate relative to the illumination device while maintaining the proximal end in an engaged relation with the illumination device a fixed distance from the light source. Two techniques are known for such coupling systems.

In a first technique, a channel is provided on the exterior surface of the illumination device to receive the proximal end of the fiber optic cable. A 360° slot is provided in the wall of the channel and a key slot is provided in the 12:00 position of the channel to provide access to the 360° slot. The key slot and the 360° slot are arranged such that during insertion of the proximal end of the fiber optic cable, a fixed protrusion provided on the proximal end of the fiber optic cable passes through the key slot into the 360° slot. During insertion, the protrusion must be located at the 12:00 position so that the protrusion passes through the key slot. Because there is nothing blocking the key slot, very little force is needed to insert the cable into the illumination device. The proximal end of the cable is then rotated in the 360° slot to move the protrusion on the cable away from the key slot. Engagement of the fixed protrusion on the proximal end of the fiber optic cable with the wall of the 360° slot maintains the proximal end of the cable in engagement with the illumination device.

There is a disadvantage with the above-described technique for securing the proximal end of the fiber optic cable to the illumination device. If the proximal end of the fiber optic cable again rotates to the 12:00 position so that the protrusion is aligned with the key slot, the proximal end of the cable can freely disengage from the illumination device with very little force. At all other positions, however, the fiber optic cable cannot be removed from the illumination device without damaging either the cable or the illumination device, because the fixed protrusion on the cable contacts the wall of the 360° slot.

In a second technique for securing the proximal end of the fiber optic cable to the illumination device, a 360° slot is provided in the proximal end of fiber optic cable. There is no key slot to provide access to the 360° slot. Instead, a protrusion is disposed on the wall of the otherwise smooth channel in the illumination device. This protrusion is retractable so that during insertion of the fiber optic cable into the illumination device, a force is required to cause the protrusion to retract. Once the proximal end of the fiber optic cable is sufficiently inserted into the channel in the illumination device, the protrusion on the illumination device is biased into an extended position by a spring so that it engages the 360° slot in the fiber optic cable to maintain the cable in engagement with the illumination device.

There is a disadvantage with this retractable protrusion technique for securing the proximal end of the fiber optic cable to the illumination device. The fiber optic cable can disengage from the illumination device if the pull-out force on the cable is large enough to cause the protrusion to retract, regardless of the rotational position of the cable relative to the illumination device. Thus, even though some pull out force is required to cause detachment of the cable from the illumination device, detachment can occur, regardless of the rotational angle of the cable relative to the illumination device, if such a pull out force is applied to the cable.

SUMMARY OF THE INVENTION

Accordingly, it is an object of the present invention to provide a phototherapy system that overcomes the shortcomings of conventional phototherapy devices to extend the lifetime of such devices. This object is achieved according to one embodiment of the present invention by providing a phototherapy system that includes a base, a carriage assembly moveably coupled to the base, and a light transmission medium that selectively couples to the base. A first light source and a second light source are coupled to the carriage assembly. The carriage assembly is moveable relative to the base such that in a first position, the first light source is coaxially aligned with a proximal end surface of the light transmission medium to illuminate this surface. When the carriage is in a second position, the second light source is coaxially aligned with the proximal end surface of the light transmission medium illuminate this surface. A sensing device determines when there is a failure of the first light source, and the carriage assembly is automatically moved from the first position to the second position once a failure of the first light source is detected, assuming that the carriage was in the first position. If the carriage was in the second position and the sensing means detects a failure of the second light source, the carriage assembly is moved to the first position.

It is a further object of the present invention to provide a coupling system for selectively securing an end portion of a light transmission medium to an illumination device that overcomes the shortcomings of the coupling systems used in conventional phototherapy devices. This object is achieved according to one embodiment of the present invention by providing a coupling system that includes a collar provided on an illumination device. The collar includes a channel therethrough that receives the proximal end portion of the light transmission medium. A rotation slot is defined in a wall of the channel, and a key slot is also defined in the wall of the channel to provide access to the rotation slot. A fixed key pin is provided on an exterior surface of the end portion of the light transmission medium. The key pin is configured to pass through the key slot and fit within the rotation slot when the proximal end portion of the light transmission medium is inserted into said channel. The key pin is also moveable within the rotation slot once the proximal end portion of the light transmission medium is inserted into the channel to permit swiveling of the proximal end portion of the light transmission medium relative to the collar. A detent pin is provided in the key slot to prevent the key pin from freely disengaging from the rotation slot. The detent pin is moveable between a first position that permits access of the key pin to the rotation slot and a second position that blocks access of the key pin to the rotation slot. Such a coupling system prevents pull out of the light transmission medium from the illumination device in nearly all rotational angles, and over only a relatively small range of angles will some amount of pull out force cause the light transmission medium to decouple from the illumination device.

It is still another object of the present invention to provide a phototherapy system that combines the advantages of the automatic lamp replacement system discussed above and the advantages of the coupling system for selectively securing an end of a light transmission medium to an illumination device in a single phototherapy system.

It is yet another object of the present invention to provide a method of treating a patient using phototherapy that does not suffer from the disadvantages associated with conventional phototherapy techniques. This object is achieved by providing a method that includes first providing a phototherapy system having a base, a carriage assembly moveably coupled to the base, a motor assembly coupled to the carriage assembly for moving the carriage assembly between a first position and a second position, a light transmission medium selectively coupled to the base in a fixed position, a first light source and a second light source coupled to the carriage assembly, and a power supply coupled to the first and second light sources. The method also includes the steps of (1) placing an operative one of the first and second light sources in an operating position in which the light source is substantially coaxially aligned with the proximal end surface of the light transmission medium, (2) energizing the light source placed in this operating position by coupling the light source to the power supply, (3) monitoring whether this light source remains operative, (3) if not, moving the other light source to the operating position, and (4) energizing this other operative light source once it is moved to the operating position.

These and other objects, features and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF THE PRESENTLY PREFERRED EMBODIMENTS OF THE INVENTION

Figure 1:
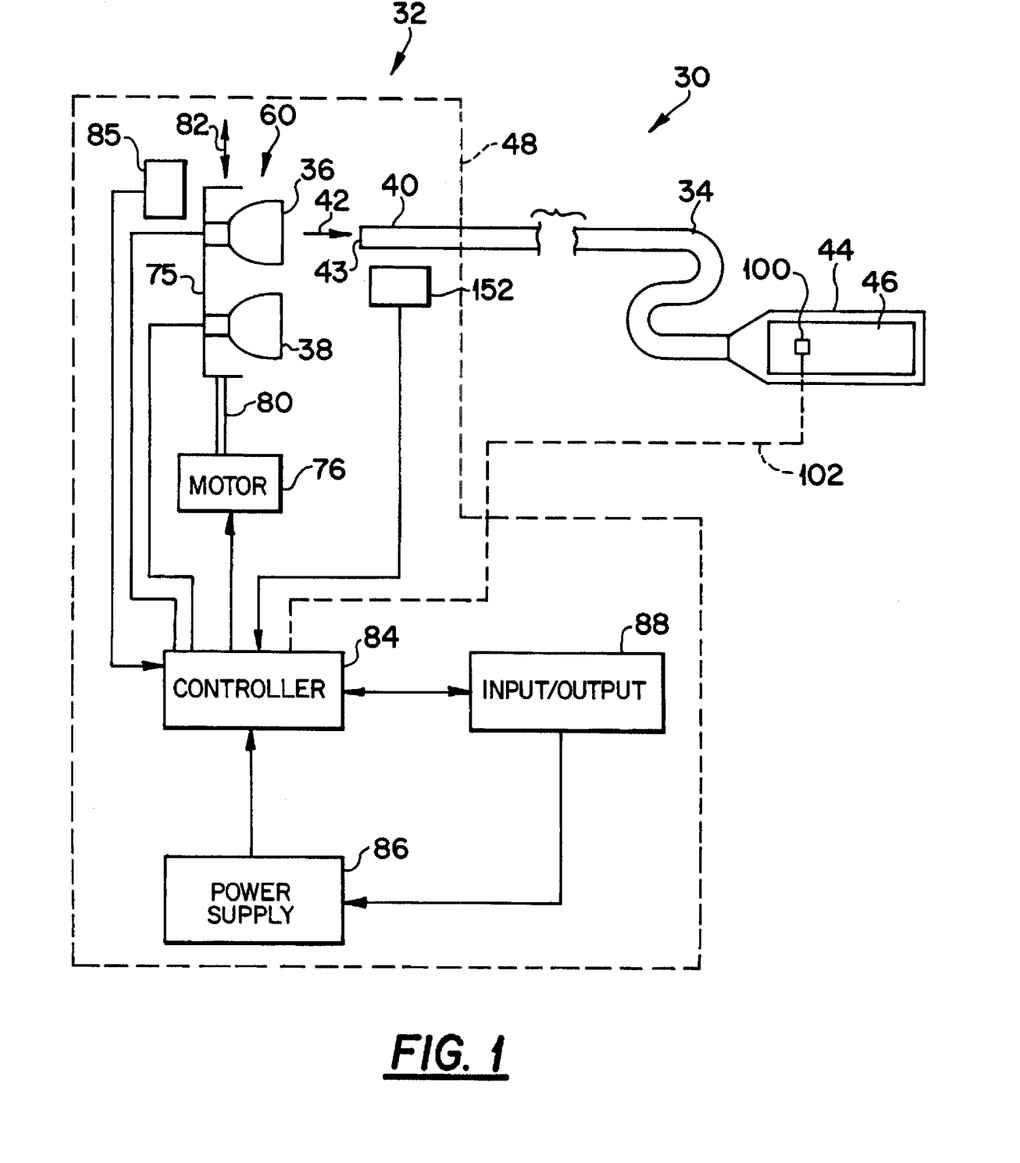
FIG. 1 is a schematic diagram of a phototherapy system according to the principles of the present invention.

FIG. 1 schematically illustrates an exemplary embodiment of a phototherapy system 30 according to the principles of the present invention. Phototherapy system 30 includes an illumination device 32 that produces a therapeutic light for illuminating the skin of the patient. Typically, the therapeutic light has a wavelength in the range of 400–550 nm. A light transmission medium 34, such as an optical fiber or plurality of optical fibers, transmits the light from illumination device 32 to a patient (not shown) so that the light can be emitted onto the patient's skin to provide its therapeutic effect. More specifically, as shown in FIG. 1, illumination device 32 of the present invention includes a first light source 36 and a second light source 38, one of which, when in a operating position, is coaxially aligned with a proximal end portion 40 of light transmission medium 34. Light flux 42 generated by the light source is directed onto a proximal end surface 43 of light transmission medium 34 and is then carried by the light transmission medium to a distal end portion 44 for emitting to the patient. Preferably, a light panel 46 is provided at distal end portion 44 for so that the therapeutic light illuminates a relatively large surface area of the patient. Although the phototherapy system of the present invention is described herein with the use of two light sources, it is to be understood that more than two light sources can be used in conjunction with light source assembly 60 without deviating from the principles of the present invention.

Figure 2:
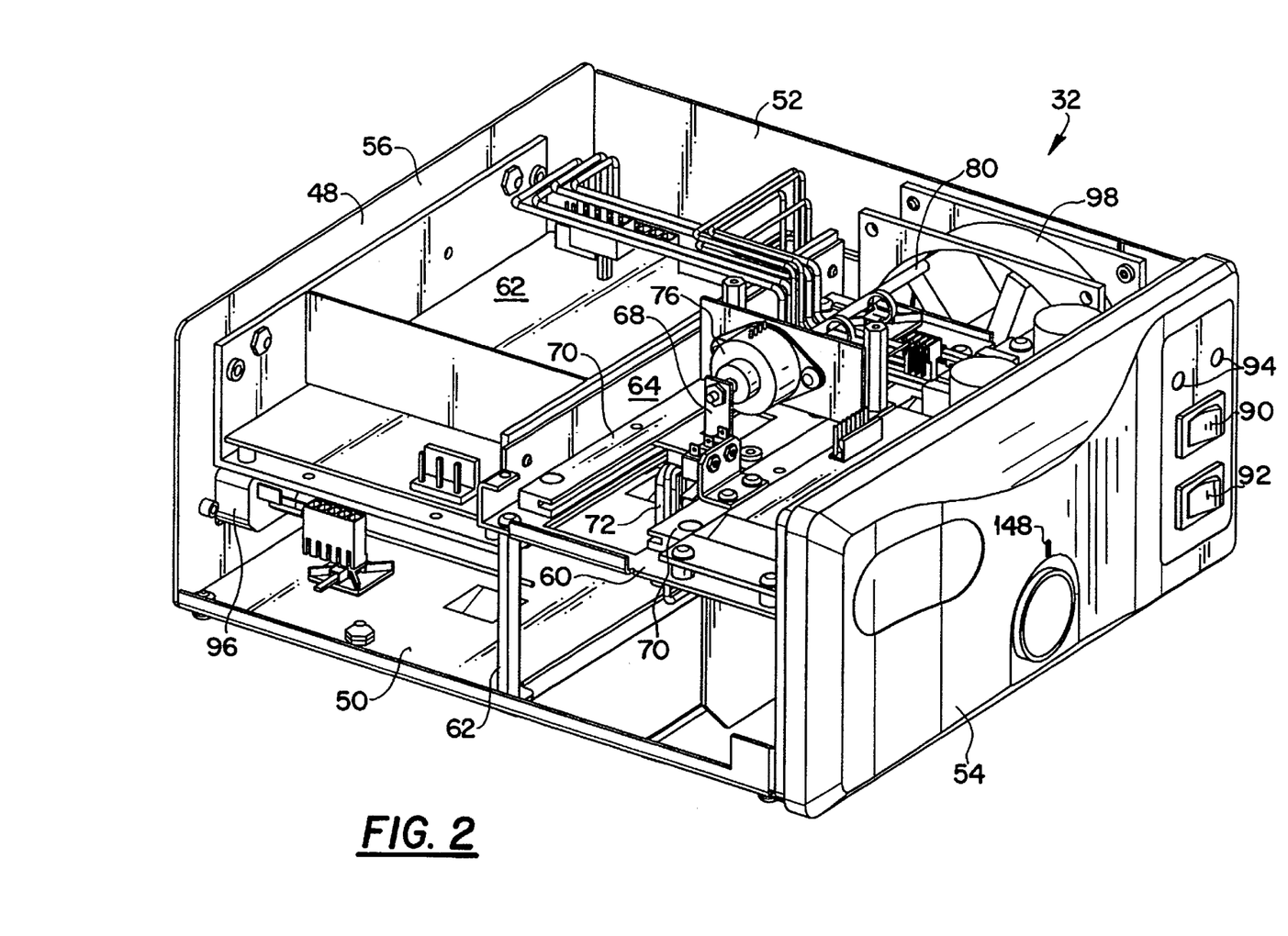
FIG. 2 is a front perspective view of the phototherapy system of FIG. 1.
Figure 3:
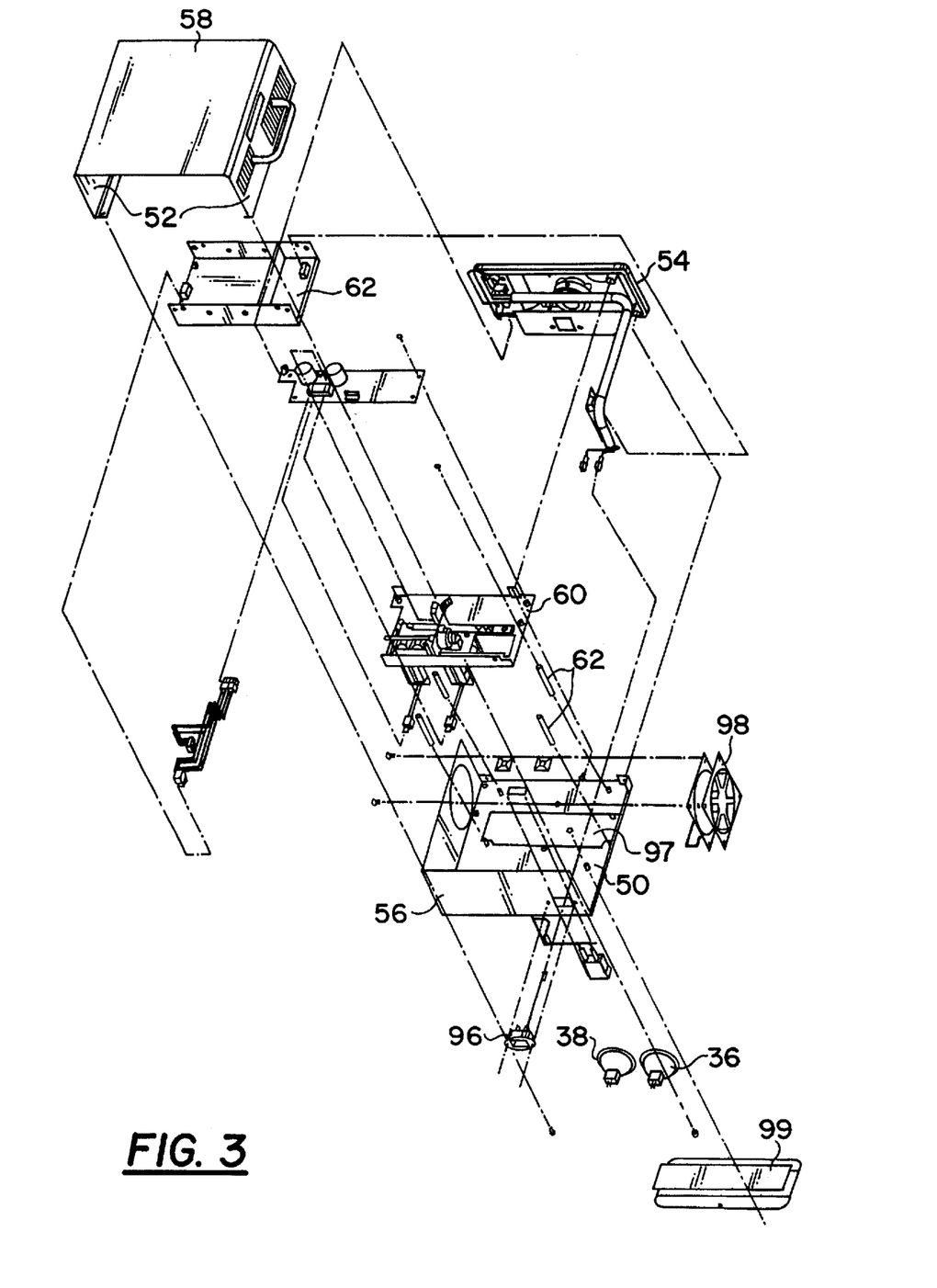
FIG. 3 is an exploded view illustrating in detail various elements of the phototherapy system of FIG. 1.

As shown in FIGS. 2 and 3, according to an exemplary embodiment of the present invention, illumination device 32 includes a housing 48 preferably defined by a base 50, side panels 52, a front panel 54, a back panel 56 and a top panel 58, all of which couple together in an assembled configuration to house the components of the illumination device, which are discussed in greater detail below. Housing 48 is schematically illustrated FIG. 1 by the dashed line encircling the components of illumination device 32. In the illustrated embodiment, light transmission medium 34 selectively attaches to front panel 54 to maintain the light transmission medium at a generally fixed position relative to the components of the housing, such as base 50. However, as discussed below, it is preferable for the proximal end portion 40 of light transmission medium 34 to rotate, i.e., swivel, relative to the housing so that the light transmission medium does not get twisted. As noted above, light transmission medium 34 carries the light produced by the illumination device to light panel 46 situation next to the patient's skin.

Figure 4A:
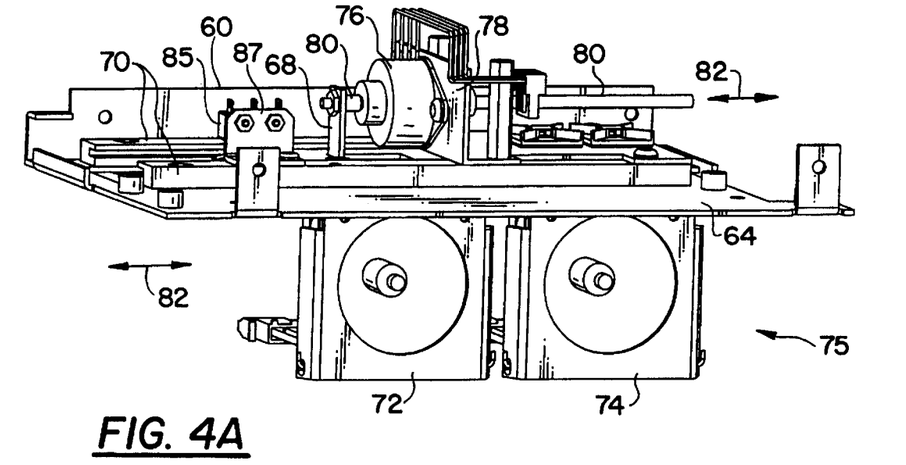
FIGS. 4A and 4B are front and back perspective views, respectively, of the light sources and carriage assembly used in the phototherapy system of FIG. 1.
Figure 4B:
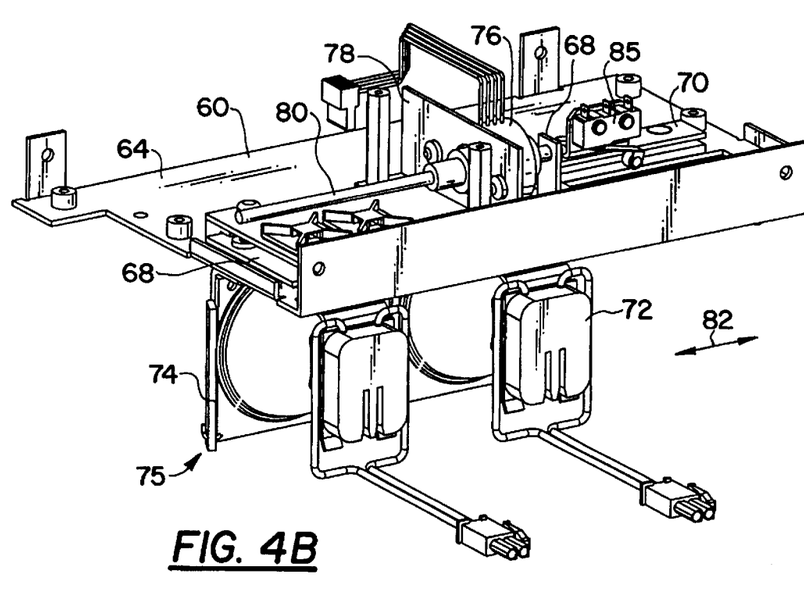
Figure 5:
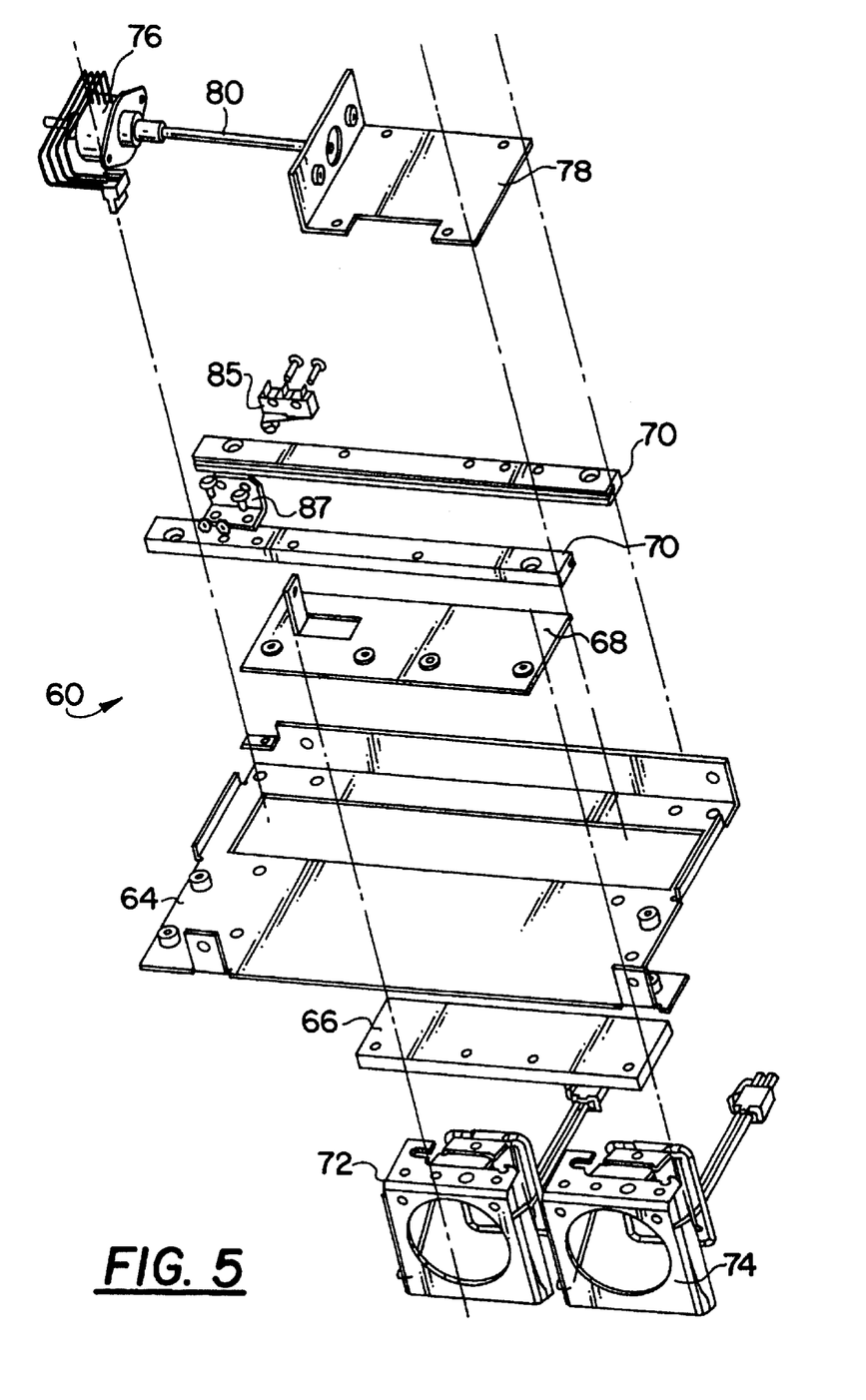
FIG. 5 is an exploded view illustrating the components of the carriage assembly shown in FIGS. 4A and 4B.

Illumination device 32 includes a light source assembly 60 and mounting members 62 that couple light source assembly 60 to the components of housing 48, including base 50. The details of an exemplary embodiment for light source assembly 60 are shown in FIGS. 4A, 4B and 5. In the illustrated embodiment, light source assembly 60 includes a chassis 64. A heat sink member 66 is slideably mounted to the chassis via a linear slide bracket 68 that moves within a pairs of slide rails 70 that are mounted on chassis 64. A first lamp holder 72 and a second lamp holder 74 are mounted to heat sink member 66 and maintain first and second light sources 36 and 38, respectively, in side-by-side relation in light source assembly 60. Linear slide rails 70 are mounted to chassis 64, with linear slide bracket 68 being moveable within rails 70, so that linear slide bracket 68, heat sink member 66, and first and second lamp holders 72 and 74 are moveable in a linear fashion relative to chassis 64.

For purposes of this disclosure, all members of the light source assembly that move relative to chassis 64 for moving the light sources relative to the housing to change the position of the first and second light sources are collectively referred to as a carriage assembly and are generally indicated in the figures by numeral 75. In the illustrated exemplary embodiment, carriage assembly 75, therefore, includes lamp holders 72 and 74, heat sink member 66 and linear slide bracket 68. It is to be understood, however, that the carriage assembly can have various configurations. For example, heat sink member 66 can be omitted or incorporated into the other members of the carriage assembly. Also, a single lamp holder that holds two or more bulbs may replace the separate lamp holders shown in the figures. The present invention further contemplates providing other geometry of the linear slide rails as well as orienting the rails in other directions, such as vertically, rather than the horizontal orientation shown in the figures. In addition, light source assembly, can be a rotary carousel configuration. However, the linear slide light source assembly is believed to be preferably in that it minimizes the amount of space required to house the lamps and provided the lamp replacement function.

A motor 76 is mounted onto chassis 64 via a mounting bracket 78, and a threaded drive rod 80 is coupled to the motor such that actuation of motor 76 rotates rod 80, thereby causing rod 80 to move in an axial direction relative to motor 76, which corresponds to the direction of slide rails 70. A portion of rod 80 is coupled to linear slide bracket 68 so that axial movement of rod 80 moves carriage assembly 75, including linear slide bracket 68, heat sink member 66, lamp holders 72 and 74, and light sources 36 and 38, in a linear direction as illustrated by arrow 82 in FIGS. 1, 4A and 4B. Motor 76 and the components of light source assembly 60 cause first and second light sources 36 and 38 to move together relative to housing 48 and relative to proximal end portion 40 of light transmission medium 34, which is coupled to the housing during operation of the phototherapy system.

Light source assembly 60 is mounted within housing 48 such that when carriage assembly 75, and, hence, light sources 36 and 38, are in a first position, which is illustrated in FIG. 1, first light source 36 is coaxially aligned with a proximal end surface 43 of light transmission medium 34. As a result, that light flux 42 from first light source 36 is focused on proximal end surface 43. In this position, the second light source is not focused on the proximal end surface of the optical fiber. Positioning the light source so that the light from the first light source is focused on the proximal end surface of the optical fiber maximizes emission of light from the first light source into the light transmission medium. In a second position (not shown), second light source 38 is coaxially aligned with proximal end surface 43 of light transmission medium 34 so that the light flux from the second light source is focused on the proximal end surface of the light transmission medium. In this second position, the first light source is not focused on the end surface of the optical fiber.

Motor 76 moves rod 80, which, in turn, moves carriage assembly 75, including first and second light sources 36 and 38, relative to the housing. In particular, rod 80 and carriage assembly 75 move in a lateral direction generally perpendicular to the optical axis of the proximal end of the light transmission medium.

As shown in FIG. 1, a controller 84 provides signals to motor 76 that cause the translational movement of the carriage assembly. Controller 84 also controls the supply of power to first and second light sources 36 and 38 so that only the light source that is in the operating position, i.e., coaxially aligned with the proximal end surface of the light transmission medium, is energized. A power supply 86 provides power to the various components of the phototherapy system, such as controller 84, light sources 36 and 38 and motor 76. In addition, an input/output system 88 communicates with controller 86 and, if desired, power supply 86.

It can be appreciated that a wide variety of mechanisms can be employed to move carriage assembly 75 between the first and second positions discussed above so that either the first or the second light source is in the operating position. In an exemplary embodiment of the present invention, motor 76 is a stepper motor that moves the carriage assembly a predetermined number of steps from a reference point to place the lamps in either the first or second position.

For example, the present invention contemplates providing a position switch 85 associated with the carriage assembly such that movement of the carriage assembly to a reference location actuates the switch. Once actuated, the location of the carriage relative to position switch 85 is known. Thereafter, the carriage assembly can be moved to either the first or second position by causing the stepper motor to advance a predetermined number of steps in a particular direction. In a preferred embodiment of the present invention, position switch 85 is mounted on one of slide rails 70 via a mounting bracket 87 such that the switch is actuated when linear slide bracket 68 is generally at a midpoint between the first and second positions. Carriage assembly 75 can then be moved to the first position by causing the stepper motor to advance a predetermined number of steps in the first direction or to the second position by causing the stepper motor to advance a predetermined number of steps in a second direction opposite the first direction.

Using a stepper motor that positions the carriage assembly based on a reference location detected by a position switch is believed to provide a relatively reliable, yet inexpensive technique for controlling the position of the carriage assembly. It is to be understood, however, that other positioning techniques are contemplated by the present invention. For example, a linear motor can be used to move the carriage assembly. In which case, stopper members can be provided on the light source assembly at appropriate locations to position the carriage assembly at the first or second position responsive to the carriage assembly being driven by the motor into the stopper. This technique, however, tends to cause a relatively large amount of wear on the drive motor. In another embodiment of the present invention, a feedback mechanism, such as switch, is provided on the light source assembly to indicate to the controller when the carriage assembly has been moved to the first or second position by the drive motor. This technique, while effective, requires additional components to provide the feedback information as well as additional processing capabilities in the controller, and, therefore, is believed to be more expensive to manufacture than the above-described stepper motor technique. The present invention also contemplates using a solenoid motor to move the carriage assembly between the two positions. In short, any motor and associated linkage that moves the carriage assembly, whether its linear or rotational movement, can be used for the present invention so long as the motor and linkage causes the carriage assembly to move to the first and second positions.

In a preferred embodiment of the present invention, input/output system 88 includes a first switch 90 for activating the power supply and a second switch 92 for changing the intensity of the light flux emitted by the lamps. Changing the intensity is accomplished by changing the amount of energy delivered to the operating lamp. In addition, the input/output system of the preferred embodiment includes one or more visible indicators 94, such as an light emitting diode (LED), that are actuated to signal various operating conditions of the phototherapy system. For example, the present invention contemplates illuminating an LED in a blinking pattern if a single bulb failure is detected and in a continuous fashion is both lamps have failed. Also, the present invention contemplates illuminating one of the LED 94 to indicate that the unit has been turned on. The present invention further contemplates that input/output system includes an audible alarm to alert the user of a condition of the phototherapy system, such as bulb failure. However, in one embodiment of the invention, the user can disable one or more of these warning functions.

It is to be understood that the present invention further contemplates more sophisticated embodiments for the input/output system. For example, a display, such as an LCD display, may be provided on a surface of the housing to provide alpha-numeric indicia to the user so that the more details on the status of the phototherapy system, for example, can be provided to the user. The audible system may provide human voice information or may be adapted to receive voice commands. Furthermore, the present invention contemplates that the input/output system include components, such as a modem or RS-232 port, to allow the controller to communicate with remote external devices so that monitoring, controlling and communicating with the phototherapy system can be accomplished from a remote site, such as a nurse's station in a hospital. In a further embodiment, the remote communication capability allows the phototherapy system to communicate with a remote location via the internet so that the system can be controlled and/or monitored by a caregiver or service provider from their operating center.

Power supply 86 is preferably a regulated power supply that operates from a external source of power (not shown). For example, FIGS. 2 and 3 illustrate a power inlet 96 that is adapted to receive AC power from a conventional source, such as a wall outlet. It is to be understood, however, that battery backup power may be provided so that therapy and/or system operation, commands and memory in controller 86 is not lost in the event of a power outage.

Other components of the phototherapy system of the present invention include a fan 98 that cools the elements within housing 48, such as the power supply and lamps. Of course, appropriate vents are provided in the housing to facilitate airflow through the housing. The present invention contemplates that fan 98 can operate continuously any time the phototherapy system is actuated or only once the temperature within the housing exceeds a predetermined threshold. In the latter situation, at least one temperature sensor (not shown) is provided in the housing to determine when the temperature in the housing exceeds the predetermined threshold. Such a sensor preferably provides an output signal to controller 84, which controls the operation of fan 98 based thereon.

As shown in FIG. 3, housing 48 preferably includes an opening 97 to provide access to first and second light sources 36 and 38. In the illustrated embodiment access opening 97 is provided in base panel 50. An access door 99 is selectively secured to close access opening 97. Access opening allows the technician to readily access the lamps without having to remove the housing. In addition, because the present invention located the good lamp in the operating position, regardless of whether the good lamp is first light source 36 or second light source 38, the technician immediately knows that the lamp not in the operating position must be the failed lamp, which is then easily replaced. This arrangement does not require the technician to determine which lamp has failed or require that the technician reset the position of the carriage assembly, as required by conventional phototherapy devices.

The present invention further contemplates providing a meter for measuring the amount of time the phototherapy system is in use. This information is important in monitoring the patient's compliance with the prescribed phototherapy, as well as monitoring the life span of the lamps. The present invention contemplates incorporating the meter into controller 84 and providing the meter such that it only measures the amount of time the lamps are actuated. This information can then be output to the user, either at the cite of the phototherapy system or at a remote cite, using the input/output system discussed above.

The present inventors also recognized that measuring the amount of time the lamps are lit may not always provide an accurate indicator of the patient's actual use of the phototherapy system. For example, the patient may leave the system running without applying the light panel on or near their skin. In which case, the compliance meter's indication the usage of the device would not correspond to the amount of time the patient actually received a therapeutic benefit from the phototherapy system. To minimize this problem, the present invention contemplates providing a device 100 to detect the presence of the patient proximate to the light panel. For example, a heat sensor, galvanic skin sensor, distance sensor, or other sensor that detects when the patient is proximate to the light panel can be incorporated into or near the light panel as device 100. The output from device 100 is provided to controller 86, as indicated by dashed line 102 in FIG. 1, and indicates when the patient is proximate to the light panel. This output can be used, for example, to control the energization of the light sources so that they are only energized when light panel 46 is proximate to a user. In addition, or in the alternative, the output from detector 100 can be used to control the operation of the compliance meter so that it only records usage time if the phototherapy system is operating and if the light panel is proximate to a user.

Figure 6:
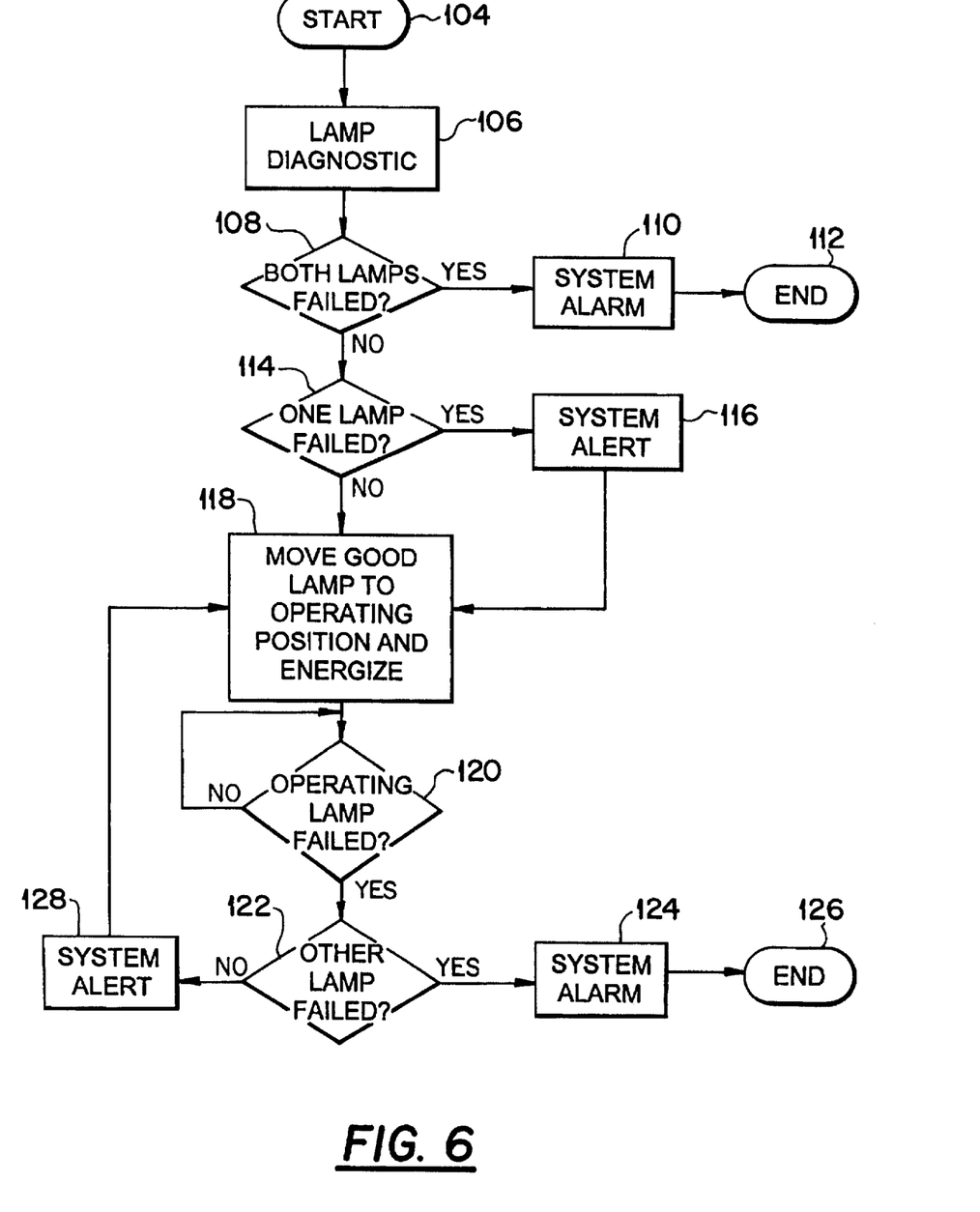
FIG. 6 is a flow chart illustrating an example of the operating procedure for the phototherapy system of the present invention.
Figure 7:
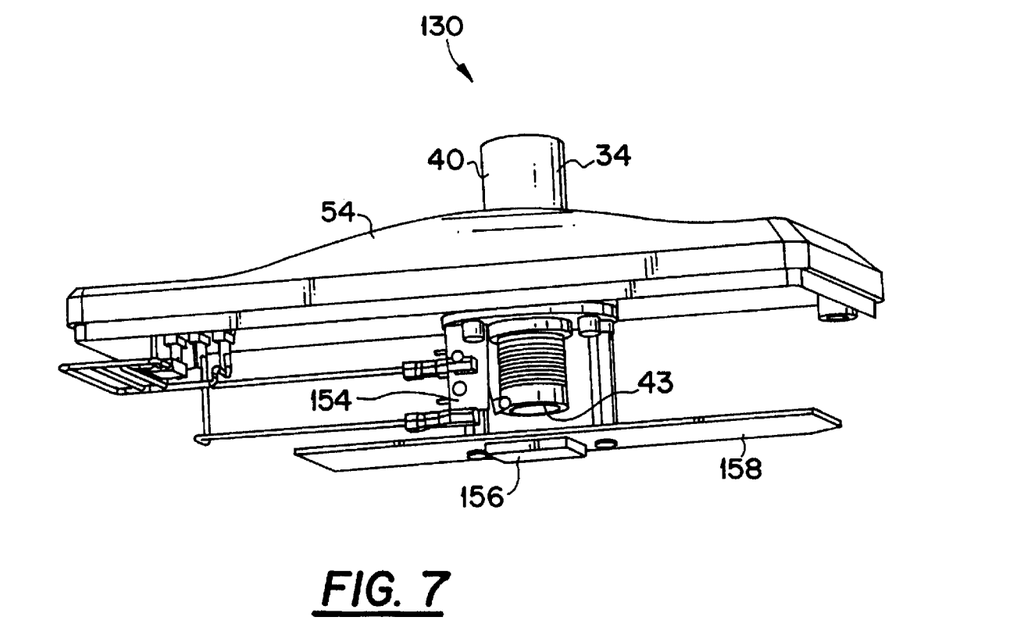
FIG. 7 is a perspective view of a coupling system used in the phototherapy system of FIG. 1.
Figure 8:
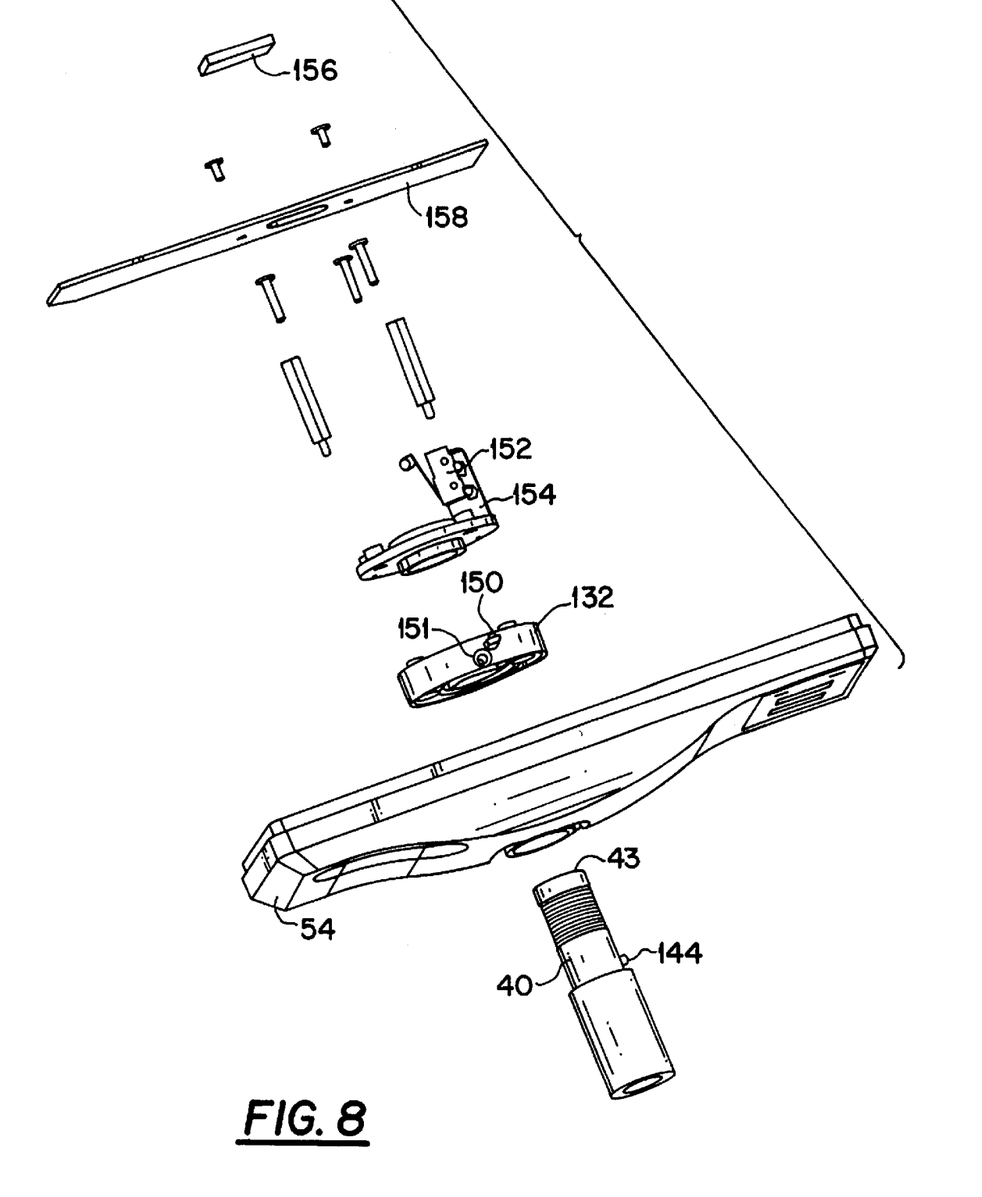
FIG. 8 is an exploded view of the coupling system of FIG. 7.
Figure 9:
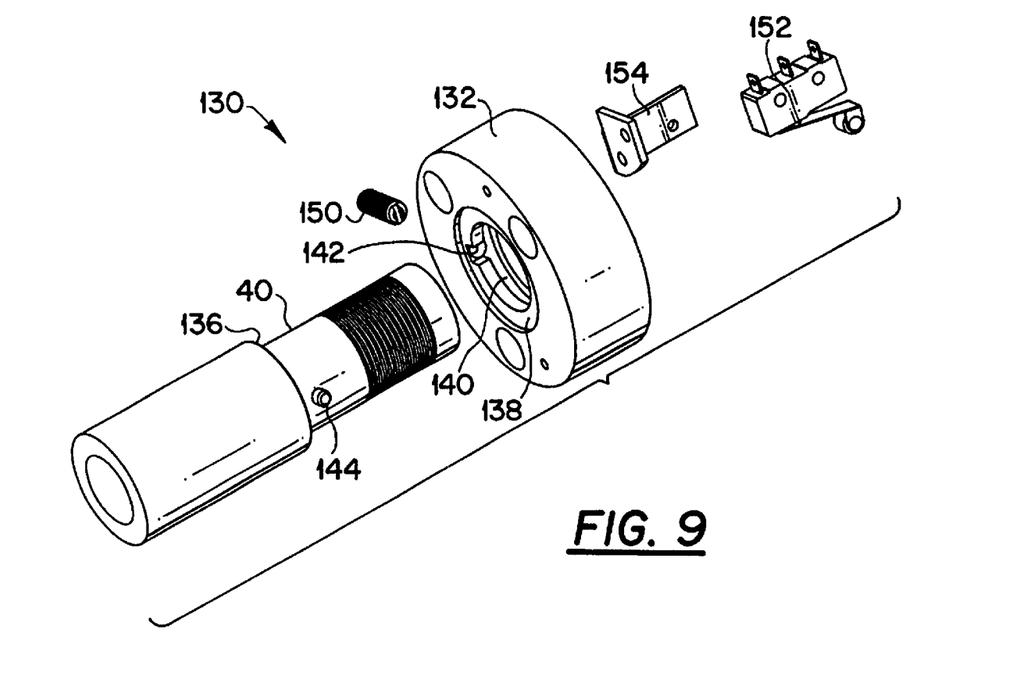
FIG. 9 is an exploded view showing various elements of the coupling system of FIG. 7 in greater detail.
Figure 10A:
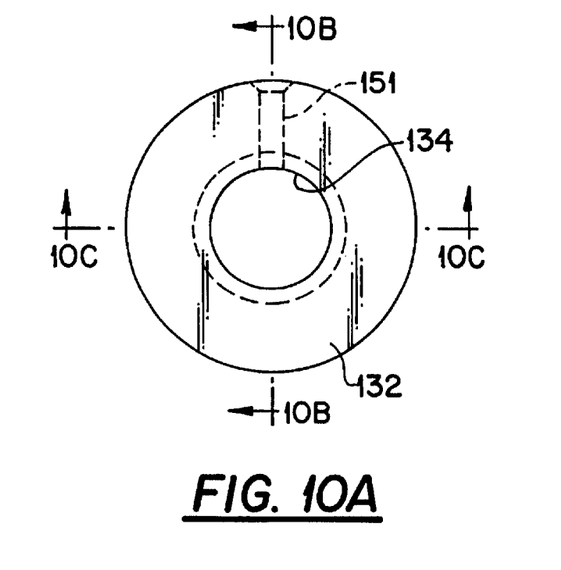
FIG. 10A is a front view of a collar used in the coupling system of FIG. 7.
Figure 10B:
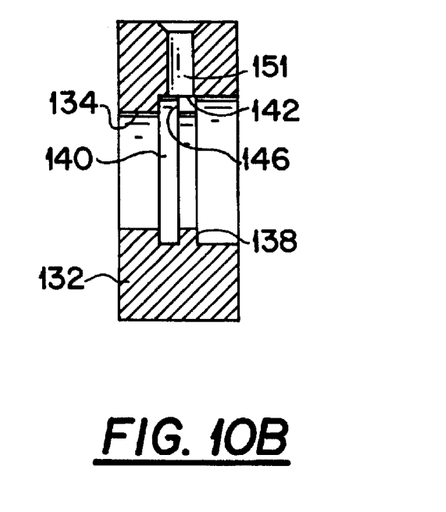
FIG. 10B is a sectional view taken along line 10B—10B in FIG. 10A.
Figure 10C:
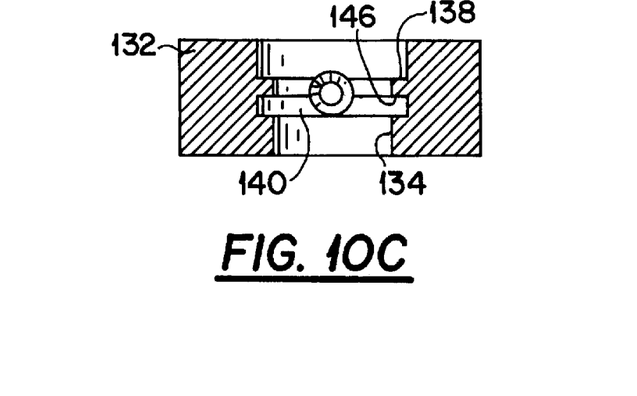
FIG. 10C is a sectional view taking along line 10C—10C in FIG. 10A.

The operation of the phototherapy system of the present invention is discussed below with reference to FIG. 6. Start up in step 104 begins when the user actuates the phototherapy system, for example, by actuating power supply switch 90 in FIG. 2. Initially, upon start up, controller 84 performs a diagnostic routine in step 106 to determine whether first and second light sources 36 and 38 are operational. In a preferred embodiment of the present invention, the lamps are tested by energizing the lamp circuit for a short duration to test the continuity of the circuit. If a lamp has failed, an open circuit would result, which is detected during the circuit continuity test. The duration that energy is provided to the lamps is preferably short enough so that no visible light is produced by the lamp as a result of being energized. The lamp does not produce light immediately upon being energized because it takes time for the lamp filament to heat up. It should be noted, that present invention contemplates using other techniques for detecting lamp failure. For example, a photo sensor can be provide near the lamp to detect whether the lamp is producing light.

If both lamps have failed in step 108, a system alarm is issued in step 110 to notify the user that the phototherapy system is not operational and the routine ends in step 112, otherwise the routine advances to step 114. In a preferred embodiment of the present invention the system alarm is issued by continuously illuminating an LED. In step 114, the controller determines whether one lamp has failed or whether both lamps are good. If one lamp has failed, the phototherapy system issues a system alert in step 116 indicating that one lamp has failed. The present invention further contemplates that this notification can also indicate which of the two lamps has failed. In a preferred embodiment of the present invention the system alert is issued by intermittently illuminating an LED. After the system alert is issued in step 116 or if both lamps are determined to be good, the good lamp is moved to the operating position so that it is coaxially aligned with proximal end surface 43 of light transmission medium 34 and is energized in step 118. If both lamps are good, one of the two lamps is selected as a default for placement in the operating position.

During operating of the phototherapy system, the controller continuously monitors in step 120 whether the lamp in the operating position has failed, e.g., burnt out, using the monitoring techniques discussed above. If the lamp has not failed, it remains lit and the phototherapy system continues to operate normally. In addition, the present invention contemplates actuating the compliance meter to keep track of the amount of time the system has been operating. If the lamp in the operating position fails, the controller determines in step 122 if the other lamp is operational. This could include testing the other lamp or recalling from memory that the other lamp has already been determined to have failed in step 114. If the other lamp is not operational, the system alarm is issued in step 124 indicating the both lamps have failed and the routine ends in step 126. If the other lamp is operative, a system alert is issued in step 128 to warn the user of the lamp failure and the good lamp is moved to the operating position and energized in step 118. Thereafter, the routine continues as discussed above. It can thus be appreciated that when the system alert is issued, the failed lamp is readily identified as being the lamp that is not in the operating position, because the operating routine of the present invention, as illustrated in FIG. 6 and discussed above, automatically places the good lamp in the operative position. Of course, if there are more than two lamps in the phototherapy system, more information must be provided in order to indicate which lamp has failed.

The details of an improved coupling system 130 according to the principles of the present invention are discussed below with reference to FIGS. 1–2 and 6–10C. As discussed above and as shown in FIG. 1, proximal end portion 40 of light transmission medium 34 selectively engages housing 48. During normal operation, the proximal end portion remains engaged to illumination device 32 so that proximal end surface 43 receives the light flux generated by the light source located in the operating position. Because distal end portion 44 of light transmission medium 34 is positioned adjacent the patient, movement of the patient tends to move the light transmission medium. For this reason, light transmission medium 34 is typically a flexible bundle of optical fibers and is preferably attached to illumination device 32 such that proximal end portion 40 can rotate relative to housing 48 while remaining securely affixed thereto. Coupling system 130 permits selective attachment of light transmission medium 34 to housing 48, allows proximal end portion 40 to rotate relative to the housing, prevents pull out of proximal end portion 40 from housing 48 over a wide range of rotational angles, and makes pull out difficult over the remaining range of rotational angles.

Coupling system 130 includes a collar 132 fixed to front panel 54, which is itself fixed to base 50. In the illustrated exemplary embodiment, collar 132 is cylindrical shaped and has a cylindrical shaped channel 134 defined therein that is sized and configured to match the size and shape of proximal end portion 40 of light transmission medium 34. More specifically, channel 134 extends along the axis of collar 132 and is configured to receive proximal end portion 40 of light transmission medium 34. It is to be understood that collar 132 and channel 134 can have a variety of configurations so long as they serve the function of coupling the proximal end portion of the light transmission medium to the housing, and, preferably, while preventing light flux from leaking from the housing. For example, channel 134 can be tapered to make it easy to insert the light transmission medium therein, so long as the smallest inner diameter of the channel provides a snug fit for the light transmission medium to minimize lateral movement of the light transmission medium and, hence, minimize light flux leakage from the housing.

In the illustrated embodiment, proximal end portion 40 of light transmission medium 34 includes a protruding rim 136 that rests against a seat 138 defined in channel 134 when the proximal end portion of light transmission medium 34 is fully inserted into collar 132. Channel 134 and proximal end portion 40 are also sized and configured to minimize lateral movement of the light transmission medium once inserted into collar 132, thereby preventing light flux from leaking from the housing. In addition, this configuration ensures that a 90° angle of incidence is maintained between the light flux and the proximal end surface of the light transmission medium and that the light source is coaxially aligned with the light transmission medium.

A rotation slot 140 is defined in a wall of channel 134 and, in a preferred embodiment, extends around the entire perimeter of channel 134. A key slot 142 is also defined in the wall of channel 134 to provide access to rotation slot 140. In the illustrated embodiment, key slot 142 is generally perpendicular to rotation slot 140. A key pin 144 is fixed on an exterior surface of light transmission medium 34. During insertion of proximal end portion 40 of light transmission medium 34 into collar 132, key pin 144 passes through key slot 142 and enters rotation slot 140. Thus, key slot 142 is sized so as to be large enough to pass key pin 144 therethrough, but is preferably as small as possible to limit the access to rotation slot 140.

Rotation slot 140 and key pin 144 are sized such that once key pin 144 is in rotation slot 140, key pin 144 is moveable along the length of rotation slot 140 to permit rotation of proximal end portion 40 of light transmission medium 34. By providing rotation slot 140 so that it extends 360° around the perimeter of channel 134 allows proximal end portion 40 of light transmission medium 34 to swivel 360° relative to front panel 54. It is to be understood, however, that rotation slot 140 need not be provided so that it extends 360° around the perimeter of channel 140 if the user is willing to forego the advantages of 360° swiveling.

A wall 146 of rotation slot 140 prevents pull out of key pin 144 from rotation slot 140. Key pin 144 and rotation slot 140 are also sized and located so as to prevents any significant lateral movement of the key pin in the rotation slot, which corresponds to movement of the light transmission medium away from and toward front panel 54. This is an important feature of the present invention in that it maintains a fixed distance between proximal end surface 43 of light transmission medium 34 and the light source in the operating position in housing 48 to keep the light flux from the light source properly focused on the end surface.

It can thus be appreciated that inserting proximal end portion 40 of light transmission medium 34 into collar 132 requires aligning key pin 144 with key slot 142 and that only once these to items are aligned, can the light transmission medium be inserted into or removed from the collar. To facilitate aligning the key pin with the key slot, a marker 148 is provided in the exterior of front panel 54. See FIG. 1. Thus, there is a limited range of rotational angles between the proximal end portion of the light transmission medium and the front panel of housing 48 in which the two can be coupled and decoupled. This range of coupling/decoupling angles corresponds to the width of key slot 142. Thus, it is preferably to make the width of key slot 142 as small as possible.

To prevent key pin 144 from freely pulling out of rotation slot 14 through key slot 142, a detent pin 150 is provided such that a portion of the detent pin selectively blocks the key slot. In an exemplary embodiment of the present invention, an access channel 151 is provided in collar 132 to allow a ball plunger screw to be inserted into that channel until the ball plunger end is located in key slot 142 to serve as detent pin 150.

Detent pin 150 is configured and arranged such that it is moveable between a first position that permits access of the key pin to the rotation slot and a second position that blocks access of the key pin to the rotation slot. Although the present invention contemplates that detent pin 150 can be manually or automatically moved between the first and second positions, in the illustrated embodiment, detent pin 150 is biased into to the second position by a biasing mechanism, such as a spring. The biasing mechanism urges detent pin 150 into the second position under a predetermined biasing force. The detent pin can be moved to the first position if the force against the pin is urging it to move to the first position greater than the predetermined biasing force. Thus, in order to insert the proximal end portion of the light transmission medium into collar 132 or to remove the collar therefrom, the push in or pull out force must be great enough to impart a force on the detent pin that overcomes the predetermined biasing force. It should be noted that the end surface of the detent pin and/or the key pin are preferably beveled to permit the key pin to impart a force on the detent pin.

In the illustrated embodiment of the present invention, coupling system 130 also includes a switch 152 that is actuated responsive to light transmission medium 34 being fully inserted into collar 132. In the embodiment illustrated in FIGS. 7–9 switch 152 is mounted on collar 132 via a mounting bracket 154. As shown in FIG. 1, switch 152 is preferably operatively coupled to controller 86 to signal to the controller when the light transmission medium is properly engaged to housing 48 and, likewise, when the light transmission medium is disengaged from the housing. Controller 86 uses this information, for example, to disable actuation of first and second light sources 36 and 38 responsive to decoupling of light transmission medium 38 from housing 48. As a result, the lifetime of the lamps is maximized and the compliance meter is does not record usage of the phototherapy system. In addition, this feature of the present invention provides a positive safety feature in that it protects users from the relatively intense light generated by the light sources that would otherwise be visible through channel 134 once the light transmission medium is disengaged from front panel 54. It is to be understood that the present invention contemplates providing switch 152 is other locations, using multiple switches and/or using sensing devices other than a mechanical switch to detect when the light transmission medium is engaged to the housing.

In the illustrated embodiment, coupling system 130 also includes a filter 156 to filter out undesired wavelengths of radiant energy, such as infrared and ultraviolet light. Preferably, filter 156 passes radiant energy between the wavelengths of 400–550 nm corresponding to the therapeutic light. A mounting bracket 158 secures filter 156 to front panel 54. It is to be understood, however, that the present invention contemplates that the wavelengths being filtered and/or passed by the filter can be varied merely by using different filters. In addition, the number and types of filters that can be used in conjunction with the coupling system, including the use of no filters, can vary depending on the desired light to be produced by illumination device 32. In addition, the specific configuration for the filter and, if being used, the method by which it is attached to the housing can vary within the scope of the present invention.

It can thus be appreciated that that present invention provides a phototherapy system that avoids the shortcomings of conventional devices in that it automatically tests the lamps and replaces a failed lamp with an operative lamp, if available, once a failure is detected and without any user intervention. In addition, the phototherapy system of the present invention provides an improved coupling system in which pull out of the light transmission medium from the illumination device is impossible over a relatively large range of rotational angles without damaging the system. For the remaining rotational angles, pull out is only possible if the pull out force is large enough to urge the detent pin to an open position. In addition, the movement of the detent pin provides positive feedback to the user indicating that the light transmission medium is fully inserted into the housing. For example, the user should be able to hear and/or feel the "click" of the detent pin popping back into the second position once the key pin is moved through the key slot into the rotation slot. By providing an interlock switch that detects when the light transmission medium is removed from the housing, the coupling system of the present invention can deactivate the light sources when the fiber optic cable is removed from the housing, thereby prevent light from escaping the housing and maximizing bulb life.

Although the invention has been described in detail for the purpose of illustration based on what is currently considered to be the most practical and preferred embodiments, it is to be understood that such detail is solely for that purpose and that the invention is not limited to the disclosed embodiments, but on the contrary, is intended to cover modifications and equivalent arrangements that are within the spirit and scope of the appended claims.

What is claimed is:

1. A phototherapy system comprising:
   (a) a base;
   (b) a carriage assembly operatively coupled to the base for movement relative to the base;
   (c) a light transmission medium selectively coupled to the base, the light transmission medium having a proximal portion adapted to receive light for transmitting through the light transmission medium and a distal portion for emitting light to a patient;
   (d) a first light source operatively coupled to the carriage assembly;
   (e) a second light source operatively coupled to the carriage assembly, the carriage assembly being moveable relative to the base such that in a first position the first light source is oriented with respect the proximal portion of the light transmission medium so as to provide light from the first light source onto the proximal portion of the light transmission medium and, in a second position the second light source is oriented with respect to the proximal portion of the light transmission medium so as to provide light from the second light source onto the proximal portion of the light transmission medium;
   (f) sensing means for sensing a failure of the first light source or the second light source;
   (g) moving means for causing the carriage assembly to move automatically from the first position to the second position responsive to the carriage assembly being in the first position and the sensing means indicating a failure of the first light source; and
   (h) a coupling system for selectively securing a proximal end portion of the light transmission medium to the base, the coupling system comprising:
      (1) a collar coupled to the base, the collar including:
         (i) a channel defined therein, the channel being configured to receive the proximal end portion of the light transmission medium,
         (ii) a rotation slot defined in a wall of the channel, and
         (iii) a key slot defined in the wall of the channel, the key slot providing access to the rotation slot;
      (2) a key pin fixed on an exterior surface of the light transmission medium, the key pin passing through the key slot and being positioned in the rotation slot responsive to inserting the proximal end portion of the light transmission medium into the channel, the key pin also being moveable within the rotation slot to permit swiveling of the proximal end portion of the light transmission medium relative to the collar; and
      (3) a detent pin provided in the key slot, the detent pin being moveable between a first position that permits access of the key pin to the rotation slot and a second position that blocks access of the key pin to the rotation slot.

2. A phototherapy system according to claim 1, further comprising a biasing mechanism that urges the detent pin into the second position while permitting the detent pin to move to the first position responsive to the key pin passing through the key slot.

3. A phototherapy system according to claim 1, further comprising means for disabling actuation of least one of the first light source and the second light source responsive to decoupling of the light transmission medium from the base.

4. A phototherapy system according to claim 3, further comprising a power supply for providing energy to the first light source or the second light source, and wherein the means for disabling actuation of the first light source or the second light source includes a switch associated with the coupling system and the power supply, the switch being positioned to provide an output responsive to removal of the proximal portion of light transmission medium from the channel to prevent the power supply from providing energy to the first light source or the second light source.

5. A phototherapy system comprising:

(a) a base;

(b) a first light source;

(c) a second light source;

(d) sensing means for determining whether at least one of the first light source and the second light source is operative;

(e) positioning means for moving the first light source and the second light source relative to the base;

(f) control means for causing the positioning means place an operative one of the first light source and the second light source in an operating position in which the operative one of the first light source and the second light source is aligned with a light transmission medium, the control means also causing the positioning means to move a remaining other operative one of the first light source and the second light source to the operating position responsive to a determination that the one of the first light source and the second light source in the operating position is not operative; and (g) means for coupling a proximal end portion of a light transmission medium to a housing including the base such that a proximal end portion of such a light transmission medium cannot be removed from the housing over a major portion of a range of rotation angles of such a proximal end portion relative to the housing, and over a remaining portion of the range of rotation angles, a predetermined amount of pull out force is necessary to disengage such a proximal end portion from the housing.

6. A phototherapy system comprising:

a housing;

a light source disposed on the housing; and means for coupling a proximal end portion of a light transmission medium to the housing such that a proximal end portion of such a light transmission medium cannot be removed from the housing over a major portion of a range of rotation angles of such a proximal end portion relative to the housing, and over a remaining portion of the range of rotation angles, a predetermined amount of pull out force is necessary to disengage such a proximal end portion from the housing.

7. A phototherapy system according to claim 6, wherein the means for coupling comprises:

a collar provided on the housing, the collar including:

a channel defined therein, the channel being configured to receive a proximal end portion of a light transmission medium, a rotation slot defined in a wall of the channel, and a key slot defined in the wall of the channel, the key slot providing access to the rotation slot; and a detent pin provided in the key slot, the detent pin being moveable between a first position that permits access of a key pin provided on an exterior surface of a proximal end portion of such a light transmission medium to the rotation slot and a second position that blocks access of such a key pin to the rotation slot, and wherein the rotation slot is sized and configured to allow movement of such a key pin along the rotation slot to permit swiveling of such a proximal end portion of a light transmission medium relative to the collar.

8. A coupling system for selectively securing a proximal end portion of a light transmission medium to an illumination device, comprising:

a collar provided on an illumination device, the collar including:

a channel defined therein, the channel being configured to receive a proximal end portion of a light transmission medium, a rotation slot defined in a wall of the channel, and a key slot defined in the wall of the channel, the key slot providing access to the rotation slot; and a detent pin provided in the key slot, the detent pin being moveable between a first position that permits access of a key pin provided on an exterior surface of a proximal end portion of such a light transmission medium to the rotation slot and a second position that blocks access of such a key pin to the rotation slot, and wherein the rotation slot is sized and configured to allow movement of such a key pin along the rotation slot to permit swiveling of a proximal end portion of such a light transmission medium relative to the collar.

9. A coupling system according to claim 8, further comprising a biasing mechanism that urges the detent pin in the second position while permitting the detent pin to move to the first position responsive to a key pin passing through the key slot.

10. A coupling system according to claim 8, further comprising means for disabling actuation of a light source in the illumination device responsive to decoupling of the light transmission medium from such an illumination device.

11. A coupling system according to claim 10, wherein the illumination device includes a power supply for providing energy to a light source, and wherein the means for disabling actuation of a light source includes a switch associated with the collar and a power supply, the switch being positioned to provide an output responsive to removal of a proximal end portion of a light transmission medium from the channel to prevent such a power supply from providing energy to such a light source.

\* \* \* \* \*